US007078584B2

(12) United States Patent
Ausubel et al.

(10) Patent No.: US 7,078,584 B2
(45) Date of Patent: Jul. 18, 2006

(54) *SALMONELLA TYPHIMURIUM*-INFECTED *CAENORHABDITIS ELEGANS* FOR IDENTIFYING INHIBITORS OF INFECTION

(75) Inventors: Frederick M. Ausubel, Newton, MA (US); Alejandro Aballay, Braintree, MA (US); Peter S. Yorgey, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/809,773

(22) Filed: Mar. 16, 2001

(65) Prior Publication Data

US 2006/0053497 A1 Mar. 9, 2006

Related U.S. Application Data

(60) Provisional application No. 60/190,186, filed on Mar. 17, 2000.

(51) Int. Cl.
*A61K 67/033* (2006.01)
*G01N 33/00* (2006.01)

(52) U.S. Cl. .................... 800/3; 800/8; 800/9
(58) Field of Classification Search .............. 800/8, 800/9, 3; 424/9.2
See application file for complete search history.

(56) References Cited

U.S. PATENT DOCUMENTS

| 4,713,378 | A | 12/1987 | Perrone et al. ............ 514/192 |
| 5,270,448 | A | 12/1993 | Payne ............................ 514/2 |
| 5,366,995 | A | 11/1994 | Savage et al. ............... 514/558 |
| 5,853,998 | A | 12/1998 | Ohno et al. ..................... 435/6 |
| 6,461,854 | B1 | 10/2002 | Ausubel et al. |
| 6,905,670 | B1 | 6/2005 | Ausubel et al. |

FOREIGN PATENT DOCUMENTS

| WO | WO 96/30053 | 10/1996 |
| WO | WO 98/12205 | 3/1998 |
| WO | WO 98/50080 | 11/1998 |
| WO | WO 98/50554 | 11/1998 |
| WO | WO 99/18996 | 4/1999 |

OTHER PUBLICATIONS

Tan et al., "Killing of *Caenorhabditis elegans* by *Pseudomonas aeruginosa* used to model mammalian bacterial pathogenesis," Proc. Natl. Acad. Sci. USA, 96: 715-720, Jan. 1999.*
Bottjer et al., "Nematospiroides dubius as a vector for *Salmonella typhimurium*," Amer. J. Veterin. Res. 39 (1): 151-153, 1978.*
Smerda et al., "Escape of *Salmonellae* from chlorination during ingestion by Pristionchus lheritieri (Nematoda: Diplogasterinae)," J. Nematol. 3 (3): 201-204, Jul. 1971.*

Aballay et al., "Programmed cell death mediated by ced-3 and ced-4 protects *Caenorhabditis elegans* from *Salmonella typhimurium*-mediated killing," PNAS 98:2735-2739 (2001).
Aballay et al., "*Salmonella typhimurium* proliferates and establishes a persistent infection in the intestine of *Caenorhabditis elegans*," Current Biology 10:1539-1542 (2000).
Alexander et al., "Surgical Infections and Choice of Antibiotics" Surgical Infections, Chapter 13:221-236 W.B. Saunders (ed) Philadelphia, PA (1991).
Bent et al., "RPS2 of *Arabidopsis thaliana:* A Leucine-Rich Repeat Class of Plant Disease Resistance Genes," Science 265:1856-1860 (1994).
Berka and Vasil, "Phospholipase C (Heat-Labile Hemolysin) of *Pseudomonas aeruginosa:* Purification and Preliminary Characterization," Journal of Bacteriology 152:239-245 (1982).
Bestwick et al., "Localization of Hydrogen Peroxide Accumulation during the Hypersensitive Reaction of Lettuce Cells to *Pseudomonas syringae* pv *phaseolicola,*"The Plant Cell 9:209-221 (1997).
Bucher, "Pathogens of Tobacco and Tomato Hornworms," Journal of Invertebrate Pathology 9:82-89 (1967).
Bulla et al., "Bacteria as Insect Pathogens," Annu. Rev. Microb. 29:163-190 (1975).
Caparon et al., "Genetic Manipulation of Pathogenic Streptococci," Methods In Enzymology 204:556-586 (1991).
Chadwick et al., "Adherence Patterns and Virulence for *Galleria Mellonella* Larvae of Isolates of *Serratia marcescens,*" Journal of Invertebrate Pathology 55:133-134 (1990).
Chadwick, "Serological Responses of Insects," Federation Proceedings 26:1675-1679 (1967).
Charpentier et al., "The Bacterial Flora of the Midgut of Two Danish Populations of Healthy Fifth Instar Larvae of the Turnip Moth, Scotia segetum," Journal of Invertebrate Pathology 32:59-63 (1978).
Cho et al., "Ornamental Plants as Carriers of *Pseudomonas aeruginosa,*" Phytopathology 65:425-431 (1975).
Cohn et al., "The Effect of Amiloride on Pigment Expression in a Clinical Isolate of *Pseudomonas aeruginosa,*" Current Therapeutic Research 51:562-567 (1992).

(Continued)

Primary Examiner—Scott D. Priebe
(74) Attorney, Agent, or Firm—Clark & Elbing LLP

(57) ABSTRACT

Disclosed are screening methods for identifying the interplay between environmental and host signals (e.g., host-dependent or host-independent signals) and physiological pathogenic pathways that control or regulate genes responsible for establishing a persistent infection, as in the colonization of the gut of the nematode.

15 Claims, 8 Drawing Sheets

OTHER PUBLICATIONS

Figure 1A:
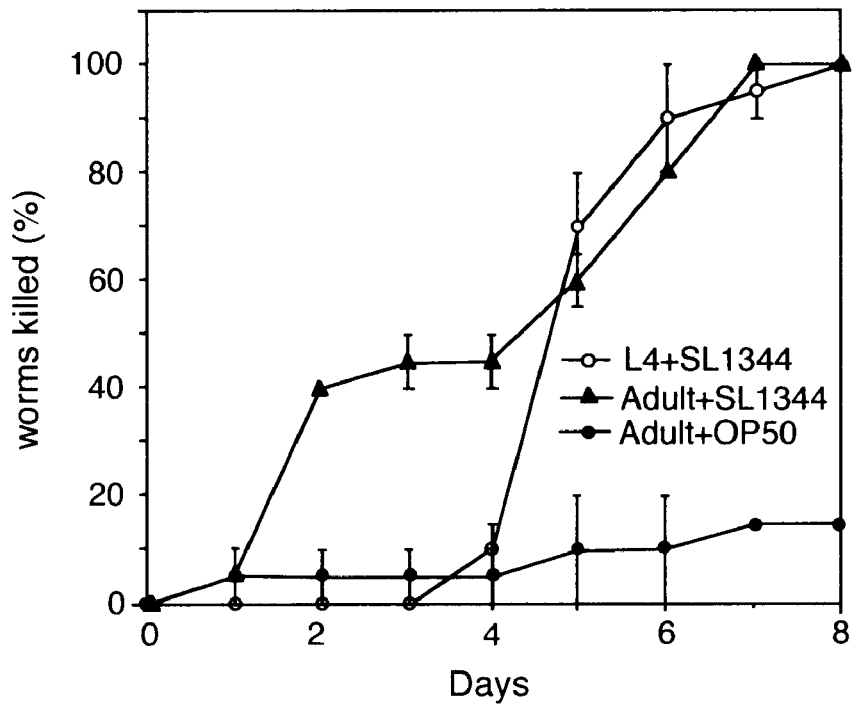

Conrad et al., "Efficacy of Aztreonam in the Treatment of Skeletal Infections Due to *Pseudomonas aeruginosa*," *Review of Infectious Research* 13:S634-S639 (1991).

Debener et al., "Identification and molecular mapping of a single *Arabidopsis thaliana* locus determining resistance to a phytopathogenic *Pseudomonas syringae* isolate," *The Plant Journal* 1:289-302 (1991).

Dong et al., "Induction of *Arabidopsis* Defense Genes by Virulent and Avirulent *Pseudomonas syringae* Strains and by a Cloned Avirulence Gene," *The Plant Cell* 3:61-72 (1991).

Dunny et al., "Pheromone-Inducible Conjugation in *Enterococcus faecalis:* Interbacterial and Host-Parasite Chemical Communication," *Journal Of Bacteriology* 177:871-876 (1995).

Dunphy, "Interaction of mutants of *Xenorhabdus nematophilus (Enterobacteriaceae)* with antibacterial systems of Galleria mellonella larvae (Insecta: Pyralidae)," *Can. J. Microbiol.* 40:161-168 (1994).

Dunphy et al., "Octopamine, a Modulator of the Haemocytic Nodulation Response of Non-immune *Galleria mellonella* Larvae," *J. Insect. Physiol.* 40:267-272 (1994).

Elrod et al., "*Pseudomonas aerugionsa*; its Role As Plant Pathogen," *Journal of Bacteriology* 46:633-645 (1942).

Elrod et al., "A Phytopathogenic Bacterium Fatal to Laboratory Animals," *Science* 94:520-521 (1941).

Fenselau et al., "Determinants of Pathogenicity in *Xanthomonas campestris* pv. *vesicatoria* are Related to Proteins Involved in Secretion in Bacterial Pathogens of Animals," *Molecular Plant-Microbe Interactions* 5:390-396 (1992).

Fuqua et al., "Quorum Sensing in Bacteria: the LuxR-LuxI Family of Cell Density-Responsive Transcriptional Regulators," *Journal of Bacteriology* 176:269-275 (1994).

Geels, "*Pseudomonas tolaasii* control by *kasugamycin* in cultivated mushrooms *(Agaricus bisporus)*," *Journal of Applied Bacteriology* 79:38-42 (1995).

Gingrich, "Acquired Humoral Immune Response of the Large Milkweed Bug, *Oncopeltus Fasciatus* (Dallas), To Injected Materials," *J. Ins. Physiol.* 10:179-194 (1964).

Gough et al., "hrp Genes of *Pseudomonas solanacearum* are Homologous to Pathogenicity Determinants of Animal Pathogenic Bacteria and are Conserved Among Plant Pathogenic Bacteria," *Molecular Plant-Microbe Interactions* 5:384-389 (1992).

Green et al., "Agricultural Plants and Soil as a Reservoir for *Pseudomonas aeruginosa*," *Appl. Microbiology* 28:978-991 (1974).

Grewal et al. "Effects of bacteria isolated from a saprophagous rhabditid nematode *Caenorhabditis elegans* on the mycelial growth of *Agaricus bisporus*," *J. Applied Bacteriology* 72:173-179 (1992).

Harshey et al., "Spinning tails: homologies among bacterial flagellar systems," *Trends in Microbiology* 4:226-231 (1996).

Hoffmann et al., "Insect Immunity: *Galleria mellonella* And Other Lepidoptera Have Cecropia-P9 Like Factors Active Against Gram Negative Bacteria," *Insect Biochem* 11:537-548 (1981).

Holloway, "Genetic Recombination in *Pseudomonas aeruginosa*," *J. Gen. Microbiol.* 13:572-581 (1955).

Huang et al., "The *Pseudomonas syringae* pv. *syringae* 61 hrpH Product, an Envelope Protein Required for Elicitation of the Hypersensitive Response in Plants," *Journal of Bacteriology* 174:6878-6885 (1992).

Huang et al., "Characterization of the *Pseudomonas syringae* pv. *syringae* 61 hrpJ and hrpI Genes: Homology of HrpI to a Superfamily of Proteins Associated with Protein Translocation," *Molecular Plant-Microbe Interactions* 6:515-520 (1993).

Iglewski et al., "NAD-Dependent Inhibition of Protein Synthesis by *Pseudomonas aeruginosa* Toxin," *Proc. Nat. Acad. Sci. USA* 72:2284-2288 (1975).

Ike et al., "Genetic Analysis of the pAD1 Hemolysin/Bacteriocin Determinant in *Enterococcus faecalis*: Tn917 Insertional Mutagenesis and Cloning," *J. Bacteriol.* 172:155-163, (1990).

Ishimoto et al., "Formation of pilin in Pseudomonas aeruginosa requires the alternative factor (RpoN) of RNA polymerase," *Proc. Nat. Acad. Sci. USA* 86:1954-1957 (1989).

Jarosz, "Interaction of *Pseudomonas aeruginosa* proteinase with the inducible non-self response of insects," *Cytobios* 83:71-84 (1995).

Jett et al., "Virulence of Enterococci," *Clin. Microbiol. Rev.* 7:462-478 (1994).

Johnston et al., "Transcriptional activation of *Salmonella typhimurium* invasion genes by a member of the phosphorylated response-regulator superfamily," *Molecular Microbiology* 22:715-727 (1996).

Kamon et al , "Immune Response of Locusts to Venom of the Scorpion," *Journal of Invertebrate Pathology* 7:192-198 (1965).

Kanost et al., "Isolation and Characterization of a Hemocyte Aggregation Inhibitor From Hemolymph of *Manduca sexta* Larvae," *Archives of Insect Biochemistry and Physiology* 27:123-136 (1994).

Kaska, "The Toxicity of Extracellular Proteases of the Bacterium *Serratia marcescens* for Larvae of Greater Wax Moth, *Galleria mellonella*," *Journal of Invertebrate Pathology* 27:271 (1976).

Kominos et al., "Introduction of *Pseudomonas aeruginosa* into a Hospital via Vegetables," *Applied Microbiology* 24:567-570 (1972).

Kovalchik et al, "*Neisseria gonorrhoeae*: Colonial Morphology of Rectal Isolates," *Applied Microbiology* 23:986-989 (1972).

Kunkel et al, "RPS2, an Arabidopsis Disease Resistance Locus Specifying Recognition of *Pseudomonas syringae* Strains Expressing the Avirulence Gene avrRpt2," *The Plant Cell* 5:865-875 (1993).

Labrousse et al., "*Caenorhabditis elegans* is a model host for *Salmonella typhimuriun*," *Current Biology* 10:1543-1545 (2000).

Laville et al, "Global control in *Pseudomonas fluorescens* mediating antibiotic synthesis and suppression of black root rot of tobacco," *Proc. Natl. Acad. Sci. USA* 89:1562-1566 (1992).

Lee, "Type III secretion systems: machines to deliver bacterial proteins into eukaryotic cells?," *Trends Microbiol.* 5:148-156 (1997).

Lemaitre et al., "The Dorsoventral Regulatory Gene Casette spätzle/Toll/cactus Controls the Potent Antifungal Response in Drosophila Adults," *Cell* 86:973-983 (1996).

Leonard et al., "*Enterococcus faecalis* pheromone binding protein, PrgZ, recruits a chromosomal oligopeptide permease system to import sex pheromone cCF10 for induction of conjugation," *Proc. Natl Acad. Sci. USA* 93:260-264 (1996).

Lysenko, "*Pseudomonas*-An Attempt at a General Classification," *J. Gen. Microbiol.* 25:379-408 (1961).

Lysenko, "The Mechanisms of Pathogenicity of *Pseudomonas aeruginosa* (Schroeter) Migula I. The Pathogenicity of Strain N-06 for Larvae of the Greater Wax Moth, *Galleria mellonella* (Linnaeus)," *Journal of Insect Pathology* 5:78-82 (1963).

Lysenko, "The Mechanisms of Pathogenicity of *Pseudomonas aeruginosa* (Schroeter) Migula II. A toxic Substance Produced in Filtrates of Cultures," *Journal of Insect Pathology* 5:83-88 (1963).

Lysenko, "The Mechanisms of Pathogenicity of *Pseudomonas aeruginosa* (Schroeter) Migula III. The Effect of N-06 Toxin on the Oxygen Consumption of Galleria Prepupae," *Journal of Insect Pathology* 5:89-93 (1963).

Lysenko, "The Mechanisms of Pathogenicity of *Pseudomonas aeruginosa* (Schroeter) Migula IV. The Antigenic Character of the Toxin Produced by Strain N-06," *Journal of Insect Pathology* 5:94-97 (1963).

Lysenko, "Chitinase of *Serratia marcescens* and Its Toxicity to Insects," *Journal of Invertebrate Pathology* 27:385-386 (1976).

Mahajan-Miklos et al., "Molecular Mechanisms of Bacterial Virulence Elucidated Using a *Pseudomonas aeruginosa-Caenorhabditis elegans* Pathogenesis Model," *Cell* 96:47-56 (1999).

Meyers et al , "Infections Caused by Microorganisms of the Genus *Erwinia,*" *Annals of Internal Medicine* 76:9-14 (1972).

Mittler et al., "Inhibition of Programmed Cell Death in Tobacco Plants during a Pathogen-Induced Hypersensitive Response at Low Oxygen Pressure," *The Plant Cell* 8:1991-2001 (1996).

Moellering, "Emergence of Enterococcus as a Significant Pathogen," *Clinical Infectious Diseases* 14:1173-1178 (1992).

Mullett et al., "Analysis of Immune Defences of the Wax Moth, *Galleria mellonella,* with Anti-haemocytic Monoclonal Antibodies," *J. Insect Physiol.* 39:897-902 (1993).

Murray, "The Life and Times of the Enterococcus," *Clinical Microbiology Reviews* 3:46-65 (1990).

Ohman et al , "Toxin A-Deficient Mutants of *Pseudomonas aeruginosa* PA103: Isolation and Characterization," *Infection and Immunity* 28:899-908 (1980).

Ostroff et el., "Identification of a New Phospholipase C Activity by Analysis of an Insertional Mutation in the Hemolytic Phospholipase C Structural Gene of *Pseudomonas aeruginosa,*" *Journal of Bacteriology* 169:4597-4601 (1987).

Pant et al, "Celluolytic Activity In A Phytophagous Lepidopteran Insect *Philosamia Ricini:* The Origin of the Enzymes," *Insect Biochem.,* 19:269-276 (1989).

Preston et al, "Rapid and Sensitive Method for Evaluating *Pseudomonas aeruginosa* Virulence Factors during Corneal Infections in Mice," *Infection and Immunity* 63:3497-3501 (1995).

Pye et al, "Hemocytes Containing Polyphenoloxidase in *Galleria* Larvae after Injections of Bacteria," *Journal of Invertebrate Pathology* 19:166-170 (1972).

Rahme et al, "Common Virulence Factors for Bacterial Pathogenicity in Plants and Animals," *Science* 268:1899-1902 (1995).

Raun et al, "Bacterial Pathogens in Iowa Corn Insects," *Journal of Insect Pathology* 5:66-71 (1963).

Reimmann et al, "The global activator GacA of *Pseudomonas aeruginosa* PAO positively controls the production of the autoinducer N-butyryl-homoserine lactone and the formation of the virulence factors pyocyanin, cyanide, and lipase," *Molecular Microbiology* 24:309-319 (1997).

Rich et al, "Genetic Evidence that the gacA Gene Encodes the Cognate Response Regulator for the lemA Sensor in *Pseudomonas syringae,*" *Journal of Bacteriology* 176:7468-7475 (1994).

Russell et al, "Antibacterial Proteins in the Midgut of *Manduca sexta* During Metamorphosis," *J. Insect Physiol.* 42:65-71 (1996).

Schroth et al, "Epidemiology of *Pseudomonas aeruginosa:* in Agricultural Areas," *Pseudomonas aeruginosa Ecological Aspects and Patient Colonization* 1-29 (1977).

Som et al, "Isolation & Identification of *Pseudomonas aeruginosa* Pathogenic to Insect Larvae," *Indian Journal of Experimental Biology* 18:590-593 (1980).

Stephens, "Bactericidal Activity Of The Blood Of Actively Immunized Wax Moth Larvae," *Canadian Journal of Microbiology* 8:491-499 (1962).

Stephens, "Immune Responses Of Some Insects To Some Bacterial Antigens," *Canadian Journal of Microbiology* 5:203-228 (1959).

Stephens et al, "Some Properties Of An Immune Factor Isolated From The Blood Of Actively Immunized Wax Moth Larvae," *Canadian Journal of Microbiology* 8:719-725 (1962).

Stevens et al, "A Quantitative Model of Invasive *Pseudomonas* Infection in Burn Injury," *Journal of Burn Care & Rehabilitation* 15:232-235 (1994).

Swift et al, "Quorum sensing: a population-density component in the determination of bacterial phenotype," *Trends Biochem. Sci* 21:214-219 (1996).

Tan et al., "*Pseudomonas aeruginosa* killing of *Caenorhabditis elegans* used to identify *P. aeruginosa* virulence factors," *Proc. Natl. Acad. Sci. USA* 96 2408-2413 (1999).

Trotter et al., "Mutants of *Enterococcus faecalis* Deficient as Recipients in Mating with Donors Carrying Pheromone-Inducible Plasmids," *Plasmid* 24:57-67 (1990).

Vlayen et al, "Identification Of The Gut Bacterial Micro Flora In Armyworms Mamestra-Brassicae Lepidoptera Noctuidae Importance Of The Environment," *Annales de la Societe Royale Zoologique de Belgique* 112:23-39 (1982).

Webster's II, New Riverside University Dictionary, The Riverside Publishing Company. Definitions of "Mushroom" and "Fungus." pp. 512 and 778 (1988).

Winans et al, "Adaptation of a conjugal transfer system for the export of pathogenic macromolecules," *Trends In Microbiology* 64:64-68 (1996).

Xu et al, "Molecular Cloning of Genes That Specify Virulence in *Pseudomonas solanacearum,*" *Journal of Bacteriology* 170:617-622 (1988).

* cited by examiner

SALMONELLA TYPHIMURIUM-INFECTED CAENORHABDITIS ELEGANS FOR IDENTIFYING INHIBITORS OF INFECTION

This application claims benefit of U.S. provisional application 60/190,186, filed on Mar. 17, 2000.

BACKGROUND OF THE INVENTION

The invention relates to screening methods for identifying pathogen virulence factors and for identifying drugs that inhibit pathogen infections.

Microbial pathogens use a variety of complex strategies to subvert host cellular functions to ensure their multiplication and survival. Some pathogens that have co-evolved or have had a long-standing association with their hosts utilize finely tuned host-specific strategies to establish a pathogenic relationship. During infection, pathogens encounter different conditions, and respond by expressing virulence factors that are appropriate for the particular environment, host, or both.

Although antibiotics have been effective tools in treating infectious disease, the emergence of drug resistant pathogens is becoming problematic in the clinical setting. New antibiotic or antipathogenic molecules are therefore needed to combat such drug resistant pathogens. Accordingly, there is a need in the art for screening methods aimed not only at identifying and characterizing potential antipathogenic agents, but also for identifying and characterizing the virulence factors that enable pathogens to infect and debilitate their hosts.

SUMMARY OF THE INVENTION

We have discovered that the microbial pathogen, *Salmonella typhimurium*, establishes a long-lasting, persistent infection in the nematode, *Caenorhabditis elegans*. This discovery enables simple screening methods for identifying the interplay between environmental and host signals (e.g., host-dependent or host-independent signals) and physiological pathogenic pathways that control or regulate genes responsible for establishing a persistent infection, as in the colonization of the gut of the nematode.

In one aspect, the invention features an isolated nematode persistently infected adult hermaphrodite worm or an L4 larval stage worm). In preferred embodiments, the isolated pathogen expresses a detectable marker; or colonizes the intestine of the nematode. In still other preferred embodiments, the pathogen is *Salmonella* (such as *Salmonella typhimurium* strain SL1344 or strain LT2).

In another aspect, the invention features a method of screening for a virulence factor that enables a pathogen to develop a persistent infection in a nematode. The method generally involves the steps of: (a) exposing a nematode to a mutagenized pathogen, a pathogen expressing a gene not normally present in the pathogen, or a pathogen overexpressing a pathogen gene; (b) determining whether the mutant or otherwise altered pathogen persistently infects the nematode, where a reduction or enhancement of disease in the nematode relative to that caused by the non-mutagenized or otherwise altered pathogen indicates a mutation in a virulence factor or a virulence factor gene that enables the pathogen to develop a persistent infection in the nematode; and (c) using the mutation or virulence factor gene as a marker for identifying the virulence factor.

Preferably, the nematode utilized in the method of screening for a pathogenic virulence factor is *Caenorhabditis elegans* (such as a one-day old adult hermaphrodite worm or an L4 larval stage worm). In preferred embodiments, the mutated or otherwise altered pathogen used for identifying the virulence factor expresses a detectable marker. In other preferred embodiments, colonization of the intestine of the nematode by the mutated or otherwise altered pathogen is decreased. In still other preferred embodiments, the pathogen used is *Salmonella* (such as *Salmonella typhimurium* strain SL1344 or strain LT2).

In yet other preferred embodiments, the method utilizes a salmonellae/*C. elegans* killing assay. In such methods, the mutated or otherwise altered pathogen has reduced or enhanced capacity to develop a persistent infection in *C. elegans*, causing less or more killing than the non-mutagenized or otherwise altered pathogen.

In another aspect, the invention features a method of screening for a compound that inhibits a persistent pathogenic infection in a nematode. The method generally involves the steps of: (a) providing a nematode persistently infected with a pathogen; (b) contacting the persistently infected nematode with a test compound; and (c) determining whether the test compound inhibits the persistent infection in the nematode.

Preferably, the nematode utilized in the compound screening method is *Caenorhabditis elegans* (such as a one-day old adult hermaphrodite worm or an L4 larval stage worm). In preferred embodiments, the pathogen used in the compound screening assay expresses a detectable marker. In other preferred embodiments, colonization of the intestine of the nematode by the pathogen is reduced. In still other preferred embodiments, the pathogen used is *Salmonella* (such as *Salmonella typhimurium* strain SL1344 or strain LT2).

In yet other preferred embodiments, the test compound is provided in a compound library; is a small organic compound; or is a peptide, peptidomimetic, or an antibody or fragment thereof.

In other preferred embodiments, the compound screening method utilizes a salmonella/*C. elegans* killing assay. In such methods, the pathogen that persistently infects *C. elegans* causes less killing in the presence of the test compound than in the absence of the test compound.

In another aspect, the invention features a method of screening for a virulence factor that enables a pathogen to develop a persistent infection in a nematode. The method generally involves the steps of: (a) exposing a nematode to a pathogen expressing a detectable marker, the pathogen being mutagenized expressing a gene not normally expressed by the pathogen, or overexpressing a pathogen gene; (b) determining whether the mutant pathogen persistently infects the nematode by measuring the level of detectable marker in the nematode, where a decrease or increase of the marker in the nematode relative to that caused by the non-mutagenized pathogen indicates a mutation in a virulence factor or a virulence factor gene that enables the pathogen to develop a persistent infection in the nematode; and (c) using the mutation or virulence factor gene as a marker for identifying the virulence factor.

In another aspect, the invention features a method of screening for a compound that inhibits a persistent pathogenic infection in a nematode. The method generally features the steps of: (a) providing a nematode persistently infected with a pathogen expressing a detectable marker; (b) contacting the persistently infected nematode with a test compound; and (c) determining whether the pathogen persistently infects the nematode by measuring the level of detectable marker in the nematode, where a decrease of the detectable marker in the nematode indicates that the test compound inhibits a persistent pathogenic infection in the nematode.

Exemplary pathogenic bacteria useful in the methods of the invention, as well as for producing persistently infected nematodes, include, without limitation, *Aerobacter, Aeromonas, Acinetobacter, Agrobacterium, Bacillus, Bacteroides, Bartonella, Bordetella, Bortella, Borrelia, Brucella, Burkholderia, Calymmatobacterium, Campylobacter, Citrobacter, Clostridium, Cornyebacterium, Enterobacter, Enterococcus, Escherichia, Francisella, Gardnerella, Haemophilus, Hafnia, Helicobacter, Klebsiella, Legionella, Listeria, Morganella, Moraxella, Mycobacterium, Neisseria, Pasteurella, Proteus, Providencia, Salmonella, Serratia, Shigella, Staphylococcus, Streptococcus, Stentorophomonas, Treponema, Xanthomonas, Vibrio,* and *Yersinia.*

By "virulence factor" is meant a cellular component (e.g., a protein such as a transcription factor or a molecule) without which a pathogen (e.g., a bacterium) is incapable of causing disease or infection in a eukaryotic host organism (e.g., a nematode or mammal). Such components, for example, are involved in the adaptation of the bacteria to a host (e.g., a nematode host), establishment of a bacterial infection, maintenance of a bacterial infection, or generation of the damaging effects of the infection to the host organism. Further, the phrase includes components that act directly on host tissue, as well as components which regulate the activity or production of other pathogenesis factors.

By "inhibits a pathogen" is meant the ability of a test compound to decrease, suppress, attenuate, diminish, arrest, or stabilize the development or progression of a pathogen-mediated disease or infection in a eukaryotic host organism. Preferably, such inhibition decreases pathogenicity by at least 5%, more preferably by at least 25%, and most preferably by at least 50% or more, as compared to symptoms in the absence of the test compound in any appropriate pathogenicity assay (for example, those assays described herein). In one particular example, inhibition may be measured by monitoring pathogenic symptoms in a nematode persistently infected with a salmonellae pathogen exposed to a test compound or extract, a decrease in the level of pathogenic symptoms relative to the level of symptoms in the host organism not exposed to the compound indicating compound-mediating inhibition of the salmonellae pathogen.

By "persistent infection" or "persistently infected" is meant an invasion or colonization of a host animal (e.g., nematode) by a pathogen (e.g., *Salmonella*) that is damaging to the host, where the size of the persistent pathogenic population that are associated with the host after the host has been transferred to a non-infectious environment remains at least 30%, preferably 50%, more preferably 80%, and most preferably 90%, or even 95% to 99% of the size of the pathogenic population before the transfer of the host to a non-infectious environment. Such an infection also includes an increase in the numbers of the pathogenic population that are associated with the host when the host is first exposed to a relatively small number of the pathogen mixed with an excess of non-pathogenic bacteria after which the host is transferred to a non-infectious environment. A persistent infection is typically measured using a nematode feeding assay (as described herein) where bacteria are assayed for their ability to establish a long-lasting association in the worm intestine.

By "detectable marker" is meant a gene whose expression may be assayed; such genes include, without limitation, β-glucuronidase (GUS), luciferase (LUC), chloramphenicol transacetylase (CAT), green fluorescent protein (GFP), and β-galactosidase.

By "isolated nematode" is meant a nematode that is purified from contaminating organisms and maintained in a culture. Exemplary nematodes (wild type or mutant), such as *C. elegans,* are obtained from publicly available sources or purified from the environment according to standard methods known in the art.

By "isolated pathogen" is meant a microbial strain that has been cultured, through the actions of man, and that elicits a disease response in a host.

The present invention provides a number of advantages. For example, the invention facilitates the identification of novel targets and therapeutic approaches for preparing therapeutic agents active on virulence factors and genes that enable a pathogen to develop a long-lasting, persistent infection in its host organism.

The invention also provides long awaited advantages over a wide variety of standard screening methods used for distinguishing and evaluating the efficacy of a compound against salmonellae pathogens. In one particular example, the screening methods described herein allow for the simultaneous evaluation of host toxicity as well as anti-salmonellae potency in a simple in vivo screen. Moreover, the methods of the invention allow one to evaluate the ability of a compound to inhibit salmonellae pathogenesis, and, at the same time, to evaluate the ability of the compound to stimulate and strengthen a host's response to salmonellae pathogenic attack.

Accordingly, the methods of the invention provide a straightforward means to identify compounds that are both safe for use in eukaryotic host organisms (i.e., compounds which do not adversely affect the normal development and physiology of the organism) and efficacious against pathogenic microbes that establish persistent infections in their hosts. In addition, the methods of the invention provide a route for analyzing virtually any number of compounds for anti-salmonellae pathogenic effect with high-volume throughput, high sensitivity, and low complexity. The methods are also relatively inexpensive to perform and enable the analysis of small quantities of active substances found in either purified or crude extract form. Furthermore, the methods disclosed herein provide a means for identifying compounds that have the capability of crossing eukaryotic cell membranes and which maintain therapeutic efficacy in an in vivo method of administration. In addition, the above-described methods of screening are suitable for both known and unknown compounds and compound libraries.

Other features and advantages of the invention will be apparent from the following description of the preferred embodiments thereof, and from the claims.

DETAILED DESCRIPTION

The drawings will first be described.

DRAWINGS

The patent or application file contains at least one drawing executed in color. Copies of this patent or patent application publication with color drawings will be provided by the Office upon request and payment of the necessary fee.

FIG. 1A shows the mechanism *C. elegans* killing by *S. typhimurium* strain SL1344. Between 10 to 20 worms were placed on each plate and each assay consisted of two replicates. L4 stage (open circle) and 1-day-old adult hermaphrodite (closed triangle and circles) worms fed either of *S. typhimurium* SL1344 (closed triangle and open circle) or on *E. coli* OP50 (closed circle). The small bars represent the standard deviations and the results are representative of at least six independent experiments.

Figure 1B:
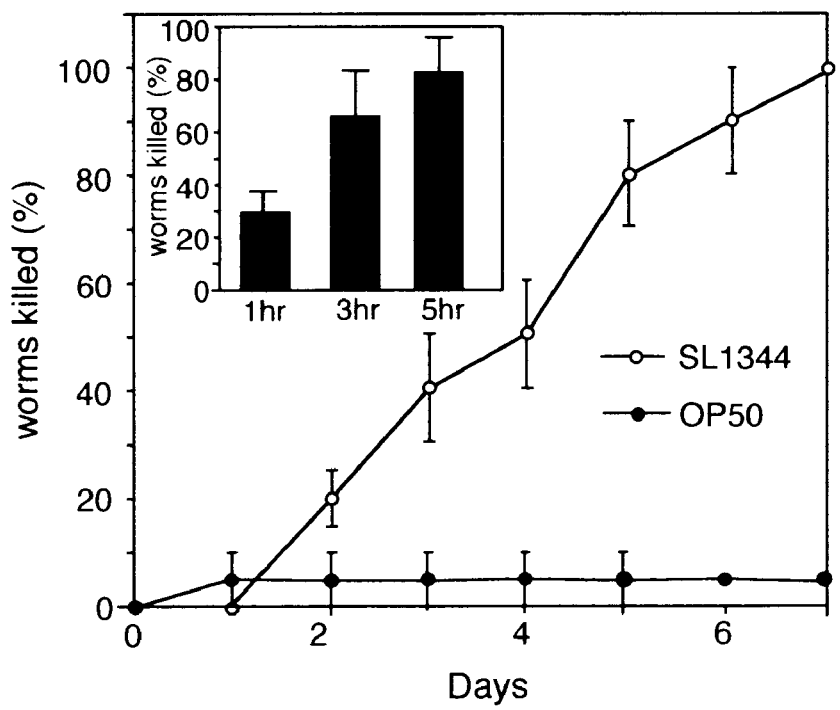
Figure 2A:
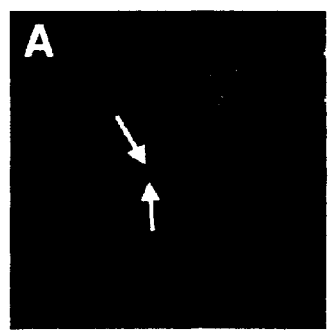
Figure 2C:
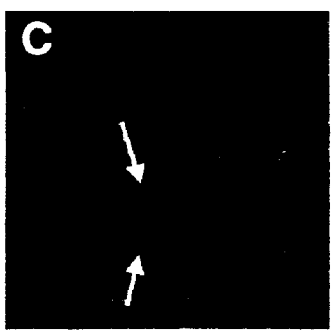
Figure 2E:
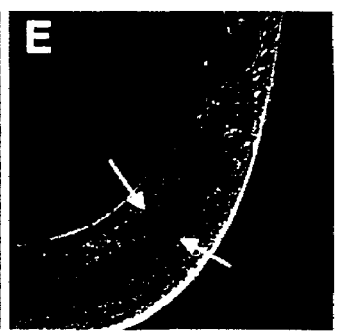
Figure 2B:
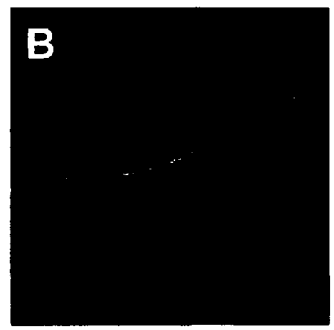
Figure 2D:
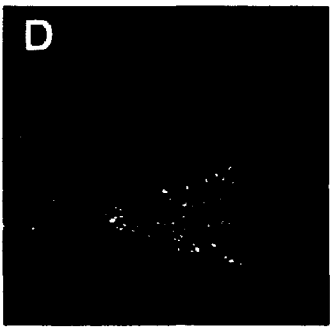
Figure 2F:

FIG. 1B shows the results of a *C. elegans* shifting experiment and the percentages of dead worms after transfer to OP50-containing plates after feeding for 5 hours on SL1344 (open circle) or on OP50 (closed circle). The small bars represent the standard deviations and the results are representative of at least three independent experiments. The insert shows the percentages of dead worms after transfer to OP50-containing plates after feeding for 1, 3, or 5 hours on SL1344. The small bars found in the insert represent the standard deviations and the results are representative of at least two independent experiments.

FIG. 2 shows confocal images of bacterial colonization of the *C. elegans* intestine. The worms were fed on *E. coli* expressing GFP (*E. coli*/GFP) (Panels A and B), *S. typhimurium* expressing GFP (*S. typhimurium*/GFP) (Panels C and D) for 72 hours, or on *P. aeruginosa* expressing GFP (*P. aeruginosa*/GFP) (Panels E and F) for 24 hours. In the transmission images (Panels A, C, and E), the intestine margins are noted with arrows. Merged images (B, D, and F) show the bacterial fluorescence (green channel) and the gut autofluorescence (red channel). The bars represent 50 µm.

Figure 3A:
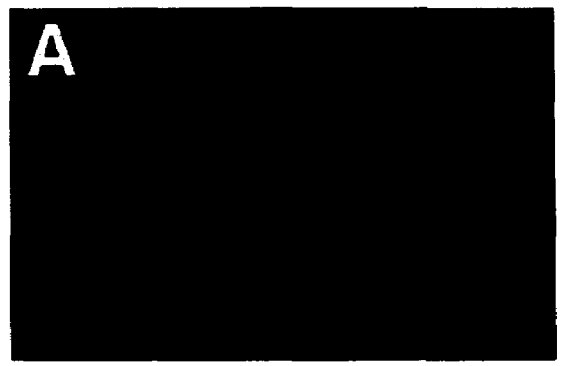
Figure 3B:
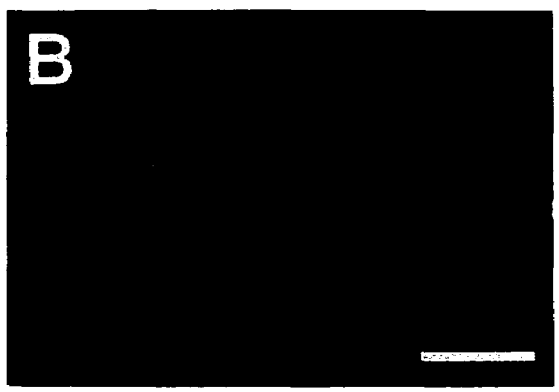

FIG. 3 shows confocal images of bacterial colonization of the *C. elegans* intestine in a shifting experiment. The worms were fed on OP50 for 24 hours after feeding on *E. coli* expressing GFP (*E. coli*/GFP) (panel A) or *S. typhimurium* expressing GFP (*S. typhimurium*/GFP) (panels B and C) for 5 hours. The merged images show the bacterial fluorescence (green channel) and the gut autofluorescence (red channel). The bars represent 50 µm.

Figure 4A:
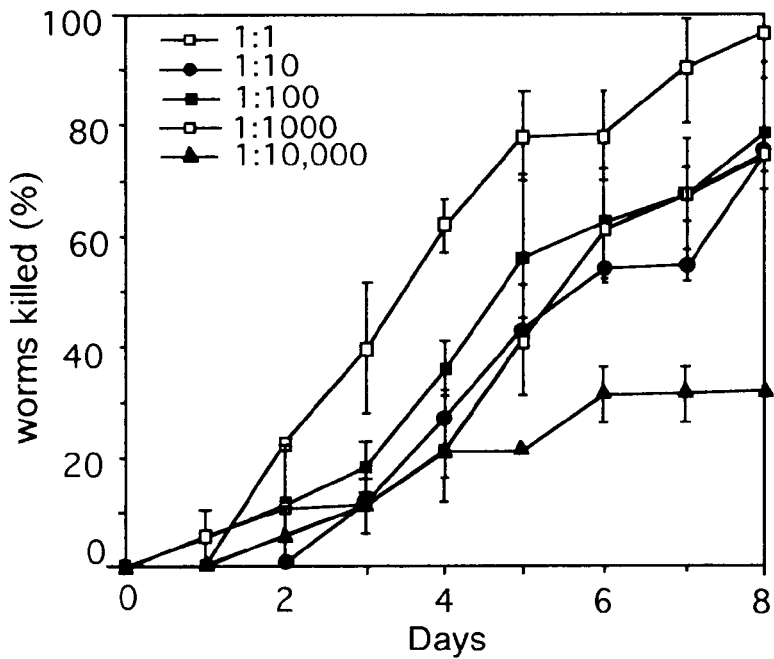

FIG. 4A shows that *S. typhimurium* proliferates in the intestine of *C. elegans*. Several dilutions of *S. typhimurium* in *E. coli* were prepared on NG plates, and 10 worms were immediately place on the plates. Each assay consisted of two replicates. After 24 hours, the worms were transferred to new plates and the amount of *Salmonella* in the plates were determined by counting colony forming units (c.f.u.) on MacConkey agar plates. The small bars represent the standard deviations and the results are representative of at least two independent experiments.

Figure 4B:
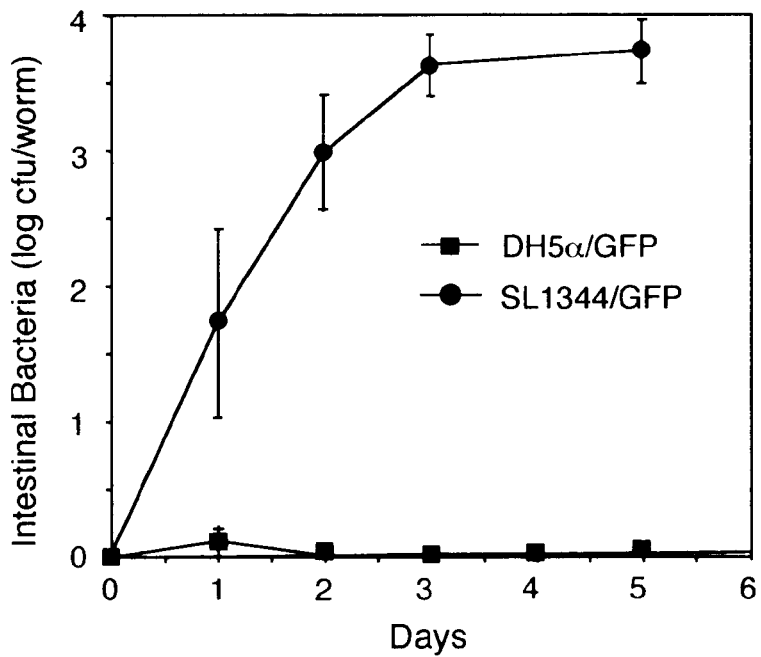

FIG. 4B shows that *S. typhimurium* proliferates in the intestine of *C. elegans*. Seventy to eighty 1-day-old adult hermaphrodite worms were placed on plates containing *S. typhimurium* expressing GFP (*S. typhimurium*/GFP) and *E. coli* not expressing GFP in a ratio of 1:10,000. In addition, the same number of worms were placed on *E. coli* expressing GFP. After 5 hours the worms were washed in M9 buffer and transferred to *E. coli* not expressing GFP plates. Subsequently, every 24 hours, 10 worms were transferred to M9 buffer containing 1% Triton X-100, and then the worms were mechanically disrupted to count the bacteria present in the gut. Bacteria were subsequently diluted in 10 mM $MgSO_4$, plated on plates containing ampicillin, and the c.f.u. counted. The data represent the means ±S.D. of two independent experiments.

Figure 5A:
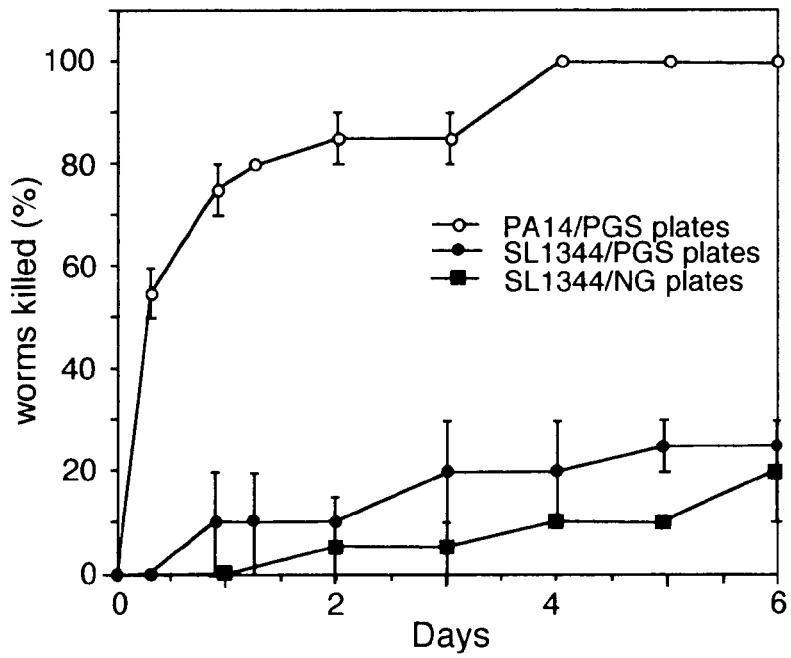

FIG. 5A shows that worm killing requires direct interaction between live *S. typhimurium* and *C. elegans*. PA14 (open circle) were grown on 0.45 µm filters placed on PGS plates, and SL1344 were grown on either PGP (closed circle) or NG plates (square). Following growth of the bacteria, filters were removed, the plates exposed to UV light for 5 minutes to kill any possible contaminating bacteria, heat-killed OP50 added as a source of food, and 20 worms were placed on each plate. Small bars represent the standard deviations and the results are representative of at least two independent experiments.

Figure 5B:
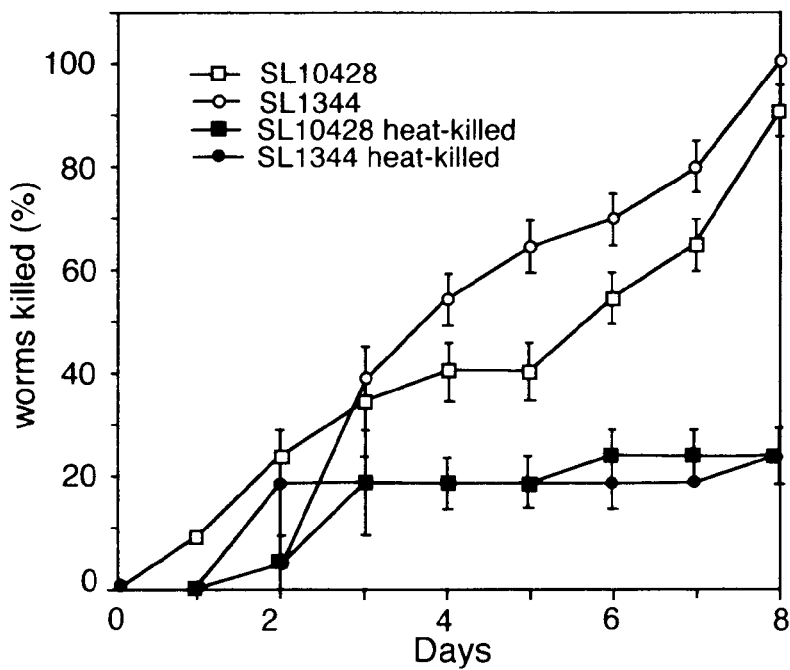
Figure 6A:
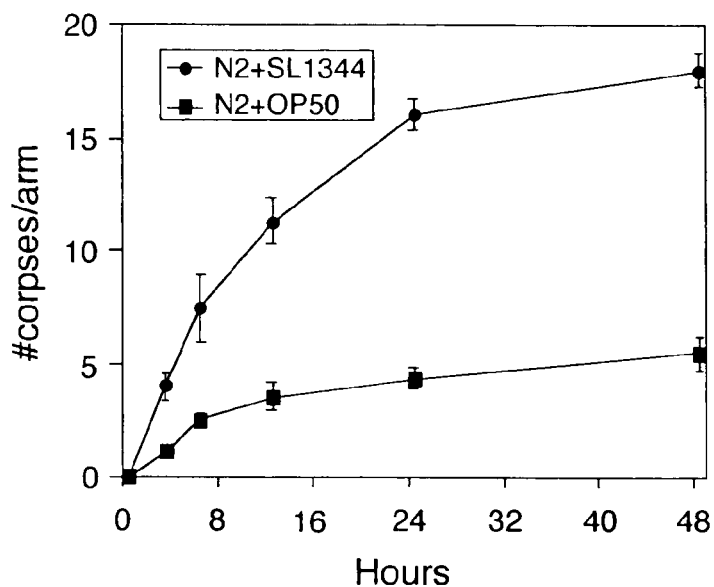
Figure 6B:
Figure 6C:
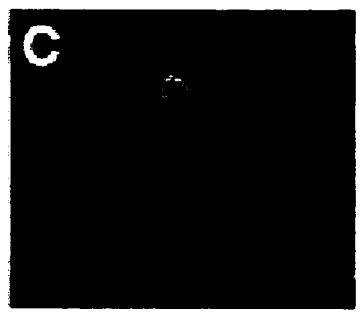
Figure 6D:
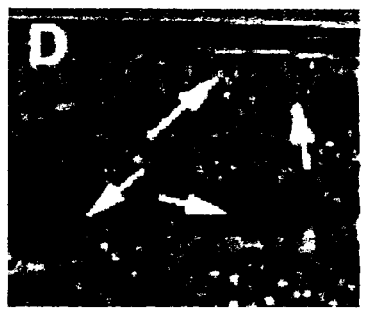
Figure 6E:

FIG. 5B shows that worm killing requires direct interaction between live *S. typhimurium* and *C. elegans*. Twenty worms feeding on heat-killed SL1344 (closed circle) or SL1344 live (open circle) and heat-killed SL14028 (closed square) or live SL14028 (open square). The small bars represent the standard deviations and the results are representative of at least two independent experiments.

FIG. 6 shows one graph (Panel A) and four photographs (Panels B—E) demonstrating that *S. typhimurium* induces programmed cell death in the *C. elegans* germline. In Panel A, cell corpses were counted over time in one gonad arm, starting with young adult animals fed on *E. coli* OP50 or *S. typhimurium* SL1344. Data (mean±SD) were from at least three independent experiments and more than 15 animals were scored at each time point. Confocal images show one-day-old hermaphrodite worms fed on *E. coli* OP50 (Panels B and C) or *S. typhimurium* SL1344 (Panels D and E) for 12 hours. In the transmission images (Panels B and D), the cell corpses are indicated with arrows. Merged images (Panels C and E) show corpses stained with SYTO 12. (Bar, 30±µm.)

Figure 7A:
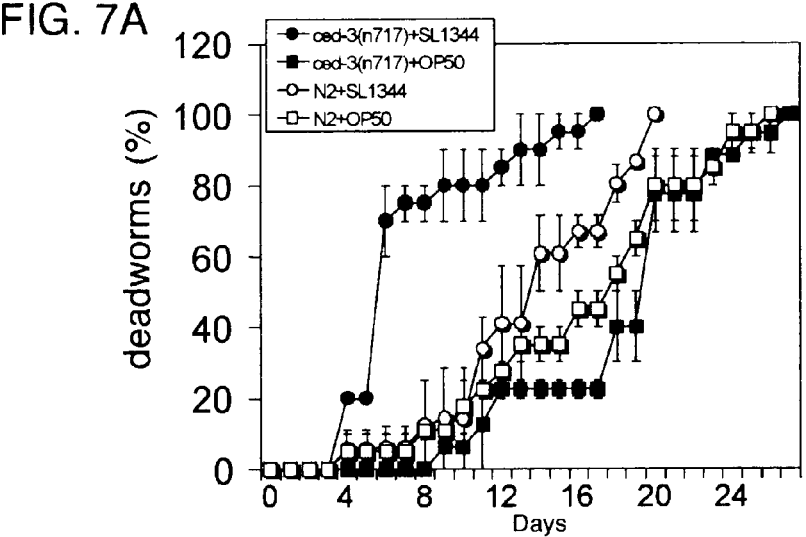
Figure 7B:
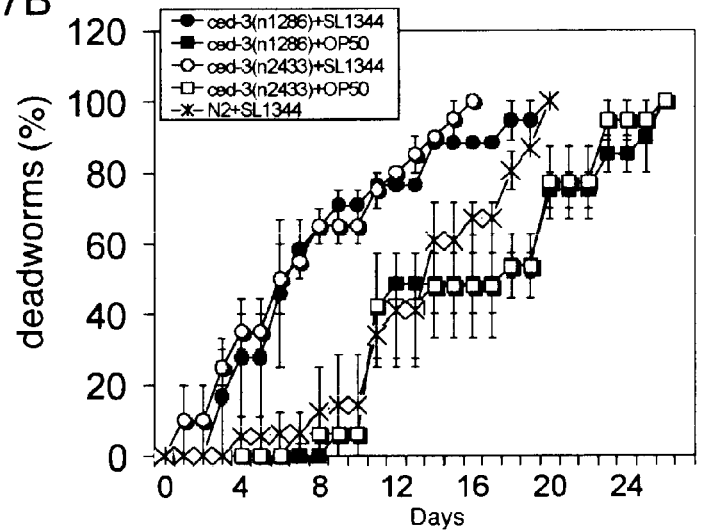
Figure 7C:
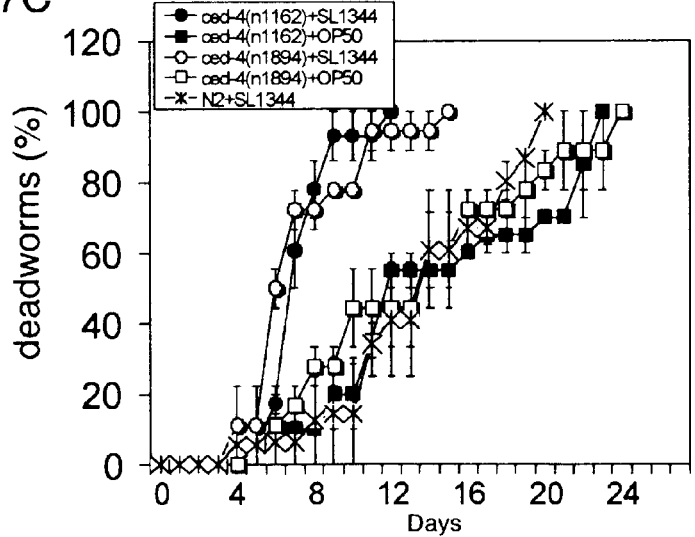

FIG. 7 shows three graphs demonstrating that ced-3 and ced-4 mutants are more susceptible to *S. typhimurium*-mediated killing. One-day-old adult animals were fed either *E. coli* or *S. typhimurium*. Panel A shows killing curves for wild type and ced-3 (n717) worms. Panel B shows killing curves for wild type, ced-3 (n1286), and ced-3 (n2433) worms. Panel C shows killing curves for wild type, ced-4 (n1162), and ced-4 (n1894) worms. More than ten animals were used in each case and data (mean±SD) were from duplicates. The results are representative of at least three experiments.

Figure 8A:
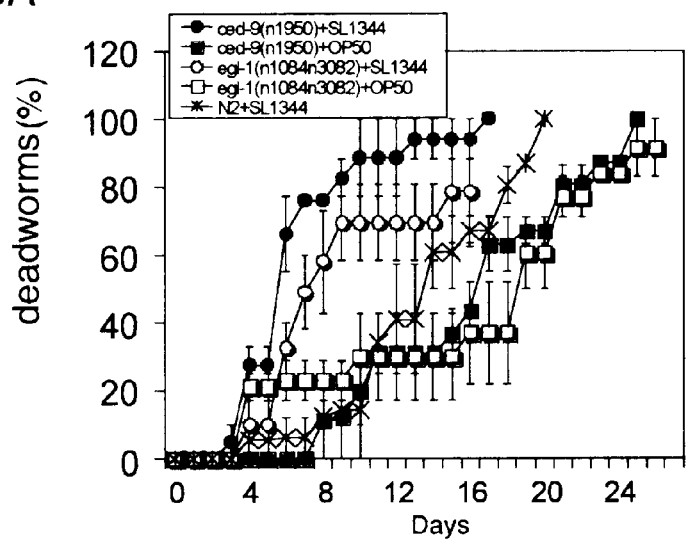
Figure 8B:
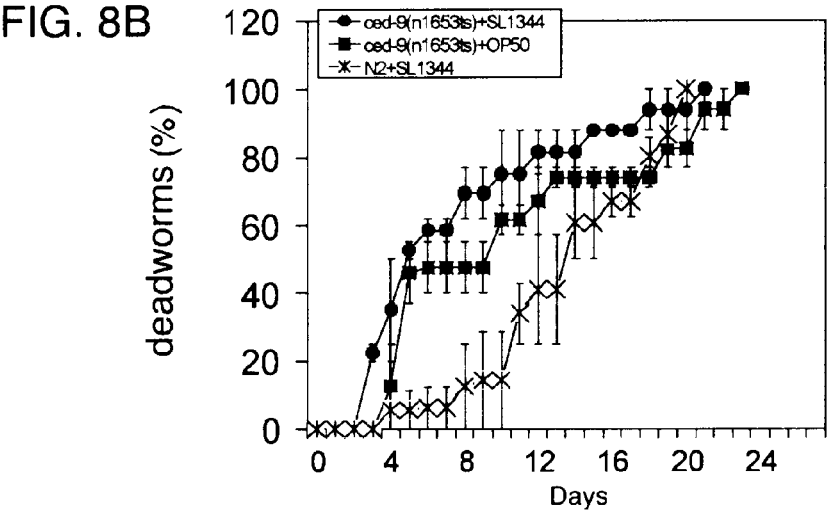
Figure 8C:
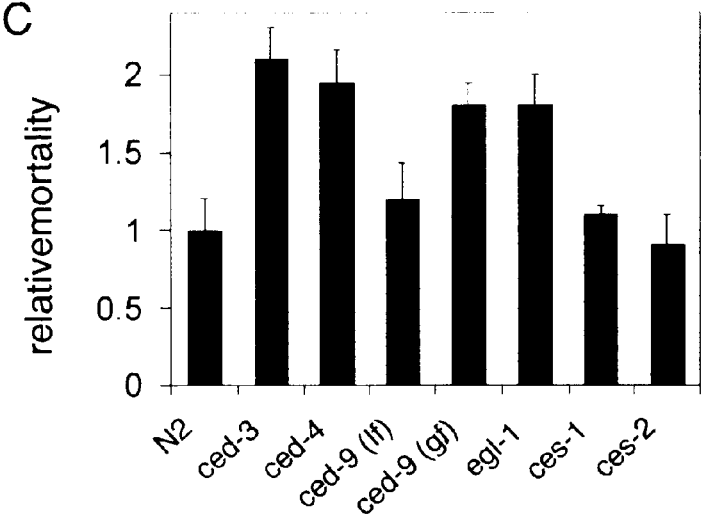

FIG. 8 shows two graphs and one histogram demonstrating that mutants deficient in stress-induced germline cell death are more susceptible to *S. typhimurium*-mediated killing. One-day-old adult animals were exposed either to *E. coli* or *S. typhimurium*. Panel A shows killing curves for wild type, ced-9(n1950)(gf) and egl-1 (n1084n3082)(lg) (gf, gain-of-function; lf, loss-of-function). Panel B shows killing curves for wild-type and ced-9 (n1653)(lf) worms. Panel C shows the relative mortality for wild type, ced-3 (n717), ced-4 (n1162), ced-9 (n1653ts)(lf), ced-9 (n1950)(gf), egl-1 (n1084n3082), ces-1 (n703), and ces-2 (n732) worms. The $LT_{50}$s were calculated in each case and the relatively mortality was calculated as described in Materials and Methods. More than ten animals were used in each case and data (mean±SD) were from three to five experiments.

Below we describe experimental evidence demonstrating that *Salmonella typhimurium* causes disease in the nematode *C. elegans* by establishing a persistent infection, including a long-lasting association in the nematode intestine, and that *C. elegans* feeding on lawns of *S. typhimurium* eventually die over the course of a few days as a result of a pathogenic process. In addition, experimental evidence is provided showing that programmed cell death (PCD) is involved in the *C. elegans* defense response to pathogen attack. The salmonellae/*C. elegans* killing assay described herein therefore provides a useful system for identifying novel virulence factors responsible for a pathogen's ability to develop a persistent infection, as well as for identifying compounds that either inhibit pathogenicity of salmonellae, promote a host's resistance to the pathogen, or both. The following experimental examples are intended to illustrate, not limit, the scope of the claimed invention.

*S. typhimurium* Kills *C. elegans* by Establishing a Long-lasting Infection

To determine if *S. typhimurium* kills *C. elegans*, worms were fed on a lawn of bacteria grown on NG agar and the time to kill 50% of the worms ($LT_{50}$) was calculated in six independent experiments. The reduced $LT_{50}$ of worms fed with *S. typhimurium* ($LT_{50}$=5.10±0.7 days) compared with the one obtained using worms fed with *E. coli* ($LT_{50}$=9.86±0.9 days), indicated that the worms were killed by *S. typhimurium* (FIG. 1A).

In addition, the physiology of the worms fed with *S. typhimurium* was different than worms feeding on *E. coli* OP50. As reported for *P. aeruginosa* infection (Tan et al., Proc. Natl. Acad. Sci. 96:2408–2413, 1999), the motility of the worms and the rate of pharyngeal pumping gradually declined, until the nematodes became immobile and died. In some cases, worms became laden with eggs, and at early times during the infections embryos hatched internally, suggesting an egg-laying defect. To study if *S. typhimurium* was capable of preventing eggs from hatching, eggs were placed in plates containing *S. typhimurium*. We observed that 95% of the eggs hatched, indicating that *S. typhimurium* does not prevent hatching under these conditions.

Since *S. typhimurium* is known for establishing a long-standing association or persistent infection with their hosts (Galán and Bliska, Annu. Rev. Cell Dev. Biol. 12:221–255, 1996), the bacterium was examined for its ability to colonize the worm intestine in an irreversible manner. The worms were fed with *S. typhimurium* for five hours, and then were transferred to plates containing *E. coli*. The results shown in FIG. 1B indicate that after 5 hours of infection *S. typhimurium* colonized the worm intestine, and that the worms died in the course of several days. The rate of killing in this shifting experiment was similar to those obtained when the *C. elegans* was in contact with *S. typhimurium* during the whole killing process. To study the time course of *S. typhimurium* infection, adult worms were allowed to feed on *S. typhimurium* for 1, 3, and 5 hours and then transferred to plates containing *E. coli*. As shown in the insert presented in FIG. 1B, the proportion of worms that survived after the transfer to *E. coli* plates was inversely proportional to the time spent feeding on SL1344. At 8 days, only 30% of the worms that had been transferred to the *E. coli* plates after feeding on SL1344 for 1 hour died. The proportion of dead worms after 8 days increased to 90% when they were fed on SL1344 for 5 hours before being transferred. In contrast, when *C. elegans* was fed on *Pseudomonas aeruginosa* PA14 for 6 hours then transferred to *E. coli*, no killing was observed within the time frame of the experiment (60 hours) (or within the normal time frame of 100% killing by feeding constantly on PA14). This result is interpreted as indicating that PA14 does not establish a lethal infection within the parameters of the experiments described for Salmonella.

The Killing Mediated by *S. typhimurium* Correlates with Proliferation of the Bacteria in the Gut To confirm that *S. typhimurium* killing involves an infectious process, we constructed a *S. typhimurium* strain expressing the *Aequorea victoria* GFP. After 72 hours of feeding on *S. typhimurium* expressing GFP, the intestinal lumen was found to be distended and full on intact bacteria, suggesting that *S. typhimurium* may be proliferating in the gut (FIG. 2, Panels B and C). Although *Pseudomonas aeruginosa* PA14 is unable to establish a long-lasting infection, similar results were obtained when the worms were fed with PA14/GFP for 24 hours (FIG. 2, Panels E and F). In contrast, no intact bacteria were observed when the worms were fed with the control *E. coli* DH5alpha/GFP strain and the lumen was not distended (FIG. 2, Panels A and B). The worms were also fed with *S. typhimurium*/GFP or *E. coli* DH5alpha/GFP for only 5 hours and then transferred to *E. coli* plates. FIG. 3 (Panels A, B, and C) shows that no *E. coli* was found in the *C. elegans* intestine after 24 hours, while *S. typhimurium* survived into the intestinal lumen. Intact *S. typhimurium*/GFP is shown at higher magnification (FIG. 3, Panel C).

To evaluate the colonization process of *S. typhimurium*, the amount of bacteria used in the feeding assays was reduced. Several dilutions of *S. typhimurium* in *E. coli* were prepared on NG plates and the worms were immediately placed on the plates for feeding. The percentage of *Salmonella* was then determined by counting the presence of c.f.u. on MacConkey agar plates. The results of these feeding experiments showed that *S. typhimurium* diluted up to 1:1,000 was capable of killing *C. elegans* at levels similar to feeding on 100% *S. typhimurium*, whereas a 1:10,000 dilution showed reduced virulence (FIG. 4A).

Since 0.1% of *S. typhimurium* supported killing, this concentration of bacteria was used to carry out a chase experiment to quantify the amount of bacteria in the lumen of the intestine during the infection. The worms were exposed for five hours to 0.1% SL1344/GFP in OP50 or to DH5alpha/GFP, and then transferred to OP50 plates. Every 24 hours 10 worms were placed in a 1.5 ml centrifuge tube and disrupted by pressing them with a pellet pestle. Dilutions of bacteria were plated and the c.f.u. counted. The results showed that after 24 hours DH5alpha/GFP practically disappeared from the worm intestine, whereas SL1344/GFP proliferated, colonizing the worm intestine (FIG. 4B).

Direct Interaction between *S. typhimurium* and *C. elegans* is Required for Killing

*P. aeruginosa* has been shown to kill *C. elegans* by the secretion of diffusible toxins referred to as "fast killing" (Tan et al., Proc. Natl. Acad. Sci. 96:2408–2413, 1999 and Mahajan-Miklos et al., Cell 96: 47–56 1999). To determine if *C. elegans* killing by *S. typhimurium* is mediated by a diffusible toxin, a killing assay was performed under fast killing conditions, using sorbitol containing plates (PGS plates). It has been shown that L4 worms died much more rapidly than adults under the *P. aeruginosa* fast killing conditions (Tan et al., Proc. Natl. Acad. Sci. 96:2408–2413, 1999), therefore, L4 stage worms were used in these experiments. *S. typhimurium* and control *P. aeruginosa* and *E. coli* were grown on 0.45 µm filters placed on the plates. The filters containing the bacteria were removed and heat inactivated *E. coli* were place as a source of food to avoid starvation (FIG. 5A). The results showed that the killing mediated by *S. typhimurium* under these conditions is not due to any diffusible toxin. FIG. 5B shows that *C. elegans* survived when fed heat-killed *Salmonella*. We have also fed the worms using the heat-killed and live *S. typhimurium* clinical isolated strain 14028. The results shown in FIG. 5B indicate that heat-killed SL14028 failed to kill *C. elegans*, and that live SL14028 killed the worms as found for SL1344.

*S. typhimurium* but not *P. aeruginosa* Elicits Germline Cell Death

As described herein, both L4 and one-day-old *C. elegans* adults died more quickly when fed on *S. typhimurium* strain SL1344 than when fed on *E. coli* strain OP50, the usual food source for growing *C. elegans*. In addition, it was observed that *S. typhimurium* infection resulted in an approximate 30%±10% decrease in brood size. To determine whether *S.*

*typhimurium* affects the rate of germline cell death, a study of germline cell apoptotic corpses was conducted with Nomarski optics or by staining with the nucleic acid stain SYTO 12 as described in Material and Methods. SYTO 12 specifically stains condensed structures in the gonad of adult hermaphrodites that are apparently the corpses of apoptotic germline cells that have undergone PCD (Gumienny et al., Development 126:1011–1022, 1999).

A higher rate of apoptosis was observed in *C. elegans* germ cells when the worms were fed *S. typhimurium* SL1344 than when fed *E. coli* OP50 (FIG. 6, Panel A and Table 1, below). The higher rate of apoptotic corpses of infected worms persisted throughout the reproductive life of the animals. The condensed structures identified as apoptotic corpses observed in worms feeding on *E. coli* (FIG. 1, Panel B) or *S. typhimurium* (FIG. 1, Panel D) were located in a region of the germline occupied by syncytial germ cells, undergoing meiosis and corresponded to the structures stained by SYTO 12 (FIG. 1, Panels E and C).

TABLE 1

Relationship between germ cell death and *Salmonella*-mediated killing

| Condition | Germ cell corpses* | n[a] | $LT_{50}$[b] |
|---|---|---|---|
| N2 + *E. coli* OP50 | 29 ± 1.8 | 20 | 16.8 ± 0.3 |
| N2 + *S. typhimurium* SL1344 | 91 ± 2.5 | 20 | 13.5 ± 1.5 |
| ced-3(n717) + *E. coli* OP50 | 0.0 | 20 | 18.8 ± 0.9 |
| ced-3(n717) + *S. typhimurium* SL1344 | 0.2 ± 0.4 | 20 | 5.8 ± 0.3 |
| ced-4(n1162) + *E. coli* OP50 | 0.0 | 15 | 13.5 ± 1.3 |
| ced-4(n1162) + *S. typhimurium* SL1344 | 0.0 | 19 | 6.9 ± 0.3 |
| ced-9(n1950) + *E. coli* OP50 | 25 ± 1.4 | 20 | 16.1 ± 0.2 |
| ced9(n1950) + *S. typhimurium* SL1344 | 29 ± 1.8 | 20 | 5.6 ± 0.2 |
| cgl-1(n1084n3082) + *E. coli* OP50 | 28 ± 0.9 | 20 | 16.9 ± 1.9 |
| cgl-1(n1084n3082) + *S. typhimurium* SL1344 | 36 ± 1.4 | 20 | 7.5 ± 1.1 |
| N2 + *S. typhimurium* SL14028 (wild type) | 75 ± 2.3 | 20 | 13.0 ± 1.0 |
| N2 + *S. typhimurium* LH954 (phoP phoQ) | 31 ± 1.7 | 20 | 16.5 ± 0.5 |
| N2 + *P. aeruginosa* PA14 | 30 ± 0.4 | 15 | 3.4 ± 0.6 |

*The germ cell corpses were scored 3 hours after the infection of young adult animals by using the vital dye Syto12 as described in Materials and Methods. The number of germ corpses per gonad arm was scored only in equally stained animals.
[a]n, number of animals count.
[b]$LT_{50}$s were calculated as described in Materials and Methods and data (mean ± SD) were from duplicates.

To evaluate whether the mere presence of *S. typhimurium* in the *C. elegans* intestine induced programmed cell death (PCD) or whether PCD requires the expression of specific virulence factors, the role of the *S. typhimurium* PhoP/PhoQ signal transduction system, a key regulator of virulence-related genes (Vescovi et al., Res Microbiol. 145:473–480, 1994) was analyzed. To this end, a *S. typhimurium* mutant (LH 954) with a phoP/phoQ/purB deletion that caused significantly less killing of *C. elegans* was utilized. The results shown in Table 1 (above) indicated that the phoP/phoQ/purB (LH 954) mutant kills *C. elegans* at a slower rate than the parental *S. typhimurium* strain (SL14028) and does not elicit an apoptotic response.

In contrast to *S. typhimurium*, when *C. elegans* was fed *P. aeruginosa* strain PA14 under either the so-called slow (Table 1) or fast (data not shown) killing conditions an elevated rate of germline cell deaths was not observed. Surprisingly, only approximately 5% of the worms that had been in contact with *P. aeruginosa* for 3 hours under the slow killing conditions were capable of taking up the SYTO 12 stain. This latter result suggests that despite the lipidic nature of the dye, an active transport may be required for the uptake of the dye and that *P. aeruginosa* blocks this process.

*S. typhimurium* Induced Germline Cell Death is Dependent on the ced-3/ced-4 Cell Death Pathway Several *C. elegans* mutants that affect PCD in somatic and germline cells were next used to determine whether the *S. typhimurium*-induced apoptosis in the germline requires previously identified apoptotic machinery and whether this apoptotic machinery is involved in *S. typhimurium*-mediated killing. The proximal cause of apoptosis in *C. elegans* is the activation of CED-3, which is required for germ cell death (Gumienny et al., Development 126:1011–1022, 1999). As shown in Table 1 (above), no germline cell deaths were observed in a ced-3 mutant feeding on *E. coli* or *S. typhimurium*. ced-3 encodes a prototypical caspase (Yuan et al., Cell 75:641–652, 1993) and CED-4 is similar to mammalian Apaf-l, an activator of caspases (Zou et al., Cell 90:405–413, 1997) that binds and activates CED-3 (Irmler et al., FEBS Lett. 406:189–190, 1997; Spector et al., Nature 385:653–656, 1997; Chinnaiyan et al., Science 275:1122–1126, 1997). Thus, if activated CED-3 is required for *S. typhimurium*-induced cell death, ced-4 mutants should also impair cell death in *Salmonella*-infected worms. As observed in ced-3 animals, no germline cell deaths were observed in ced-4 mutants feeding on *S. typhimurium* lawns (Table 1, above).

*C. elegans* ced-3 and ced-4 Mutants Are Hypersusceptible to *S. typhimurium*-mediated Killing As shown in FIG. 7 (Panels A and B), ced-3 mutants died much more quickly than wild-type worms when feeding on *S. typhimurium,* but died at the same rate as wild-type worms when feeding on *E. coli.* The $LT_{50}$s for one-day-old hermaphrodite nematodes when fed at 20° C. on *S. typhimurium* was 14 days for wild-type worms compared to 5.9, 6.6, and 6.5 days (respectively) for three different ced-3 mutants alleles, whereas the $LT_{50}$ for the three ced-3 mutants feeding on *E. coli* was 19, 16, and 16 days (respectively) compared to 17 days for wild-type worms feeding on *E. coli.* In addition, the rate at which wild-type worms died when feeding on *S. typhimurium* ($LT_{50}$=14 days) was faster than the rate at which both wild-type worms ($LT_{50}$=17) and ced-3 mutant worms ($LT_{50}$=19, 16, 16 days) died when feeding on *E. coli* (for example, see FIG. 7, Panel A). Two different ced-4 mutants were also more susceptible to *S. typhimurium*-mediated killing (FIG. 2, Panel C). The fact that three ced-3 alleles and two ced-4 alleles exhibited the same phenotype when feeding on *S. typhimurium* makes it unlikely that enhanced susceptibility is caused by secondary mutations or the effect of a particular allele on a process unrelated to cell death. Consistent with the observation that *P. aeruginosa* does not induce a high level of germline PCD, ced-3 and ced-4 mutants were not more susceptible to *P. aeruginosa*-mediated fast or slow killing (data not shown). These experiments, therefore, are consistent with the conclusion that CED-3 and CED-4 are involved in a *C. elegans* defense response to *S. typhimurium* but not to *P. aeruginosa*.

The *C. elegans* Upstream Regulators of Cell Death CED-9 and EGL-1 are also Involved in *S. typhimurium*-induced Germline Cell Death CED-9 is a member of the Bcl-2 family of cell death regulators (Hengartner et al., Nature 356:494–499, 1992) that directly inhibits CED-4, apparently by sequestering CED-4 and proCED-3 in an inactive ternary complex called the apoptosome (Hengartner, Nature 388:714–715, 1997). The ced-9 (1950) gain-of-function mutant has a similar phenotype to ced-3 and ced-4 loss-of-function mutants with respect to PCD in developing worms EGL-1 is thought to activate the PCD cascade by inhibiting CED-9 (Conradt et al., Cell 93:519–529, 1998). Consistent with the results described in the previous section, Table 1 (above) shows that Salmonella-induced apoptosis is substantially reduced in the ced-9(n1950) mutant. Similarly, the egl-l(n1084n3082) loss of function mutant also exhibited a reduction in Salmonella-induced germline apoptosis compared to wild-type N2 worms (Table 1, above). Moreover, both the ced-9(n1950) and the egl-l(n1084n3082) mutants were more susceptible to Salmonella-mediated killing (FIG. 8, Panels A and C).

Consistent with previous observations that ced-9 loss of function mutants exhibit a much higher rate of spontaneous cell death than wild-type worms (Gumienny et al., Development 126:1011–1022, 1999), the ced-9(n1653ts) loss of function mutant exhibited elevated PCD in the gonads (data not shown). FIG. 8 (Panel B) shows that the ced-9(n1653ts) mutant had a short lifespan when feeding on S. typhimurium. On the other hand, it also had a short lifespan when feeding on E. coli. Therefore, the relative mortality of ced-9 worms feeding on S. typhimurium [defined as: ($LT_{50}$ of wild type worms feeding on S. typhimurium/$LT_{50}$ ced-9 on S. typhimurium)/($LT_{50}$ wild type worms on E. coli/$LT_{50}$ ced-9 on E. coli)] was not significantly different than control wild-type worms as illustrated in FIG. 8 (Panel C). The short lifespan of the ced-9 mutant is most likely related to the fact that loss of function mutations in ced-9 cause sterility and maternal-effect lethality as a consequence of ectopic cell death (Henfartner et al., Nature 356:494–499, 1992).

Figure 3C:

Mutations in the genes ces-1 and ces-2 affect a specific subset of somatic programmed cell deaths (Ellis et al., Development 112:591–603, 1991) but have not been shown to be involved in germline cell death (Gumienny et al., Development 126:1011–1022, 1999). As expected, these mutants were not more susceptible than wild-type worms to Salmonella-mediated killing (FIG. 3C).

The above-described results demonstrate that S. typhimurium colonization of the C. elegans intestine leads to an increased level of cell death in the worm gonad and that C. elegans PCD mutants are more susceptible to S. typhimurium-mediated killing. These results suggest that S. typhimurium virulence factors trigger somatic signals that induce the PCD pathway and that induction of the PCD pathway serves a protective role when C. elegans encounters an adverse environmental stimulus such as the attack of a potentially pathogenic bacterium. These conclusions are consistent with the following observations. First, when C. elegans are colonized by S. typhimurium, the intestinal lumen of infected animals is distended and full of intact bacteria, but no bacteria are found beyond this region or in contact with the gonads. Second, C. elegans PCD-related mutants, including several loss of function alleles of ced-3 and ced-4 and a gain of function allele of ced-9, do not exhibit S. typhimurium-elicited PCD (Table 1, above) and are more susceptible to S. typhimurium-mediated killing (FIGS. 2 and 3). Third, a pleiotropic S. typhimurium phoP/phoQ mutant that fails to synthesize a variety of virulence-related factors does not elicit germline cell death (Table 1, above).

In contrast to S. typhimurium, P. aeruginosa does not elicit PCD in C. elegans germ cells and C. elegans PCD-related mutants do not exhibit an aberrant phenotype in response to P. aeruginosa compared to wild-type worms. A major difference between the P. aeruginosa and S. typhimurium infection models is that a small inoculum of S. typhimurium can proliferate in the intestine of C. elegans and establish a persistent and lethal infection even in the presence of a large excess of E. coli cells, whereas P. aeruginosa only accumulates in the intestine when it is the sole source of food. Factors that allow S. typhimurium to proliferate in and colonize the intestine may correspond to specific C. elegans receptors that in turn may be involved in the elicitation of the PCD response.

In addition, the above-described results show that in response to S. typhimurium infection, PCD eliminates excess germ cells in the C. elegans gonad that could be detrimental to the worms and that this PCD process may be involved in the C. elegans defense response to environmental insults, such as pathogen attack. These findings indicate that PCD is an ancient host defense mechanism that can be readily dissected using the power of C. elegans genetic and genomic analysis.

Materials and Methods

The above-described results were obtained using the following materials and methods.

Bacterial Strains, Plasmids, and Growth Conditions

The P. aeruginosa strain PA14 (Rahme et al., Science 268:1899–1902, 1995), PA14/GFP strain (Tan et al., Proc Natl Acad Sci USA 96:715–720, 1999), S. typhimurium strain SL1344 (Hoiseth, Nature 291, 238–239, 1981), SL1344/GFP (thus work), S. typhimurium clinical isolated strain 14028 (SL14028) were kindly provided by E. Hohmann, Escherichia coli strain DH5alpha (Bethesda Research Laboratories), DH5alpha/GFP strain (Tan et al., Proc Natl Acad Sci USA 96:715–720, 1999), and Escherichia coli strain OP50 (Brenner, Genetics 77, 71–94, 1974) were grown at 37° C. in Luria Broth (LB) media. The SL1344/GFP strain was made using the construct pSMC21-GFP (Bloemberg et al., Appl. Environ. Microbiol. 63:4543–51, 1997). S. typhimurium 14028 (Angelakoupoulos wt al., Infect. Immun. 68:2135–2141, 2000) and S. typhimurium LH954 (20) were grown overnight at 37° C. in Luria Broth (LB). The C. elegans mutants used were derived from the wild-type variety Bristol N2. ced-3 (n717) and ced-9 (n1653ts) mutants were kindly provided by Michael Hengartner, Cold Spring Harbor Laboratory, ced-3 (n1286), ced-3 (n2433), ced-4 (n1162), ced-4 (n1894), egl-l (n1084n3082), ces-1 (n703), and ces-2 (n732) were obtained from the Caenorhabditis Genetics Center, University of Minnesota, St. Paul, Minn.

Maintenance of the Nematodes

The nematodes were maintained as hermaphrodites at 20° C., grown on standard plates and fed with Escherichia coli strain OP50 as described by Sulston and Hodgkin (In: the Nematode Caenorhabditis elegans, ed., W.B. Wood, Cold Spring Harbor Lab. Press, Plainview, N.Y., pp. 587–606, 1988). Worms were observed under a dissecting microscope (Leica MZ6).

Bacterial Infection Assays

The killing assays were conducted by spreading 10 µl of bacterial culture grown overnight in LB on nematode growth (NG; modified from nematode growth medium agar described in Sulston and Hodgkin (In: the Nematode Caenorhabditis elegans, ed., W.B. Wood, Cold Spring Harbor Lab. Press, Plainview, N.Y., pp. 587–606, 1988); using 0.35% instead of 0.25% peptone or peptone-glucose-sorbitol (PGS; 1% Bacto-Peptone/1% NaCl/1% glucose/0.15 M sorbitol/1.7% Bacto-Agar) media for nematode killing assays (3.5 cm diameter plates). After spreading the bacterial culture, plates were incubated at 37° C. for 12 hours and then ten to twenty worms were placed on the assay plate, which was then incubated at 25° C. When required, the bacteria were killed by heating at 60° C. for 90 minutes. The *E. coli* strain OP50 was used as a control for the assays. Worm mortality was scored over time, and a worm was considered dead when it failed to respond to touch. Any worms that died as a result of getting stuck to the wall of the plate were excluded from the analysis. The time to kill 50% of the nematodes (LT50) was calculated using the PRISM (version 2.00) computer program using the equation: Y=Bottom+ (Top−Bottom)/(1+10^((LogEC50-X)*HillSlope)), where X is the logarithm of days and Y is the average of killed worms; Y starts at Bottom and goes to Top with a sigmoid shape. The relative mortality of worms feeding on *S. typhimurium* was calculated with the equation: Relative mortality=($LT_{50}$ wild type *C. elegans* on *S. typhimurium*/$LT_{50}$ *C. elegans* mutant on *S. typhimurium*)/($LT_{50}$ wild type *C. elegans* on *E. coli* $LT_{50}$ *C. elegans* mutant on *E. coli*).

*C. elegans* Shifting Experiments

Eighty to one-hundred one-day-old adult hermaphrodite worms were seeded on bacteria lawns and allowed to feed. After 1, 3, or 5 hours, the worms were transferred to plates containing *E. coli* OP50. Before transfer, worms were washed two times in M9 buffer, transferred to plates containing OP50 for two hours and then transferred to new plates containing OP50. Every 24 hours the worms were transferred to new plates and the c.f.u. counted. To count the c.f.u., 10 worms were washed in M9 buffer and transferred to a 1.5 ml tube with M9 buffer containing 1% Triton X-100 where they were mechanically disrupted using a pellet pestle. Dilutions of bacteria were made in 10 mM $MgSO_4$, plated on ampicillin containing plates or in MacConkey agar base plates, and the c.f.u. counted.

Confocal Microscopy

The worms were seeded on DH5alpha/GFP or SL1344/GFP lawns. After 5 hours, one half the total number of worms was transferred to plates containing *E. coli* OP50 as described above. For each time point, five worms were placed on a pad of 1% agar in PBS and 30 μM sodium azide in M9 buffer was used as anesthetic. The experiments were repeated at least four times and confocal imaging was performed using a Leica TCS SP confocal microscope. Composite images were assembled and edited using Adobe PhotoShop 5.0.

Cell Corpse Assay

To quantify the number of apoptotic germ cells, the animals were stained with SYTO 12 (Molecular Probes, Eugene, Oreg.) as previously described (Gumienny et al., Development 126:1011–1022, 1999). Briefly, the worms were incubated in 5 μM SYTO 12 for 3–4 hours at room temperature and then seeded on bacterial lawns to reduce the amount of stained bacteria in the gut. After 20–30 minutes, animals were mounted in a drop of M9 salt solution containing 30 mM NaN3 and observed using a Leica TCS SP confocal microscope. Only animals that were brightly and equally stained were scored.

Nematode Screening Systems For Identifying Virulence Factors Establishing Persistent Infections Based on the results described above showing that *Salmonella* establishes a persistent infection in the nematode. *C. elegans*, we have developed methods for identifying virulence determinants important for establishing this type of infection. The screen, in general, utilizes the above-described pathogen/nematode killing assays and exploits the ability to screen thousands of randomly generated mutant pathogens. In addition to using wild type host worms in the screening assays, mutant worms that are constipated or defecation defective, such as aex-2 and unc-25, mutants that are grinding defective, such as phm-2 and eat-14, and specific ABC transporter mutants such as pgp-4 and mrp-l, or any of the other mutants described herein may be utilized as well.

In general, a pathogen is assayed (using the method described herein) for its ability to establish a persistent infection in a nematode. Once identified, the pathogen, such as *Salmonella typhimurium* strain SL1344, is mutated according to standard methods known in the art and then subsequently evaluated for its ability to induce disease by establishing a persistent infection in the nematode host organism. A mutagenized pathogen found to have diminished ability for establishing a persistent infection is useful in the method of the invention. Such mutant pathogens are then used for identifying host-dependent or host-independent virulence factors responsible for establishing the persistent infection according to methods known in the art.

Other screening assays for identifying and characterizing virulence factors include constitutive or overexpression of putative virulence genes from *Salmonella* or other bacterial species. Examples would be constitutively expressing a putative transcription factor or repressor on a plasmid in the pathogen, such as *Salmonella typhimurium* strain SL1344, and testing these altered pathogens for enhanced or reduced virulence in *C. elegans*. Alternatively, a plasmid library of clones covering the entire *Salmonella typhimurium* (or other pathogen) genome, could be screened for enhancement or suppression of Salmonella virulence in *C. elegans*. The results of these screens identify virulence factors, and subsequently provide valuable information as to their downstream targets.

The following is a working example of a virulence factor nematode screening system which utilizes the human clinical isolate *S. typhimurium* strain SL1344 identified as persistently infecting the gut of *C. elegans*. The advantage of using a nematode as a host for studying microbial pathogens is the relative simplicity of identifying non-pathogenic mutants in the nematode system.

In one preferred working example, in which survival is monitored, four to eight *C. elegans* worms (e.g., one-day old adult hermaphrodites) are placed on a lawn of a mutagenized strain of a pathogen, and survival is monitored after approximately five hours according to the methods described herein. For example, a pathogen, such as *Salmonella typhimurium* strain SL1344, is mutated according to any standard procedure, e.g., standard in vivo or in vitro insertional/transposon mutagenesis methods (see, e.g., Kleckner et al., *J. Mol. Biol.* 116: 125, 1977 or Simon et al., Gene 80 (1):161–169, 1989). Other methods are also available, e.g., chemical mutagenesis, or directed mutagenesis of DNA. Very few or no live worms are found on plates seeded with wild-type, pathogenic *S. typhimurium* strain SL1344, whereas on a plate with mutagenized *S. typhimurium* strain SL1344, increased survival (e.g., as determined by an increased $LT_{50}$) of the worms is observed. Thus, the ability of worms to grow in the presence of mutated *S. typhimurium* strain SL1344 is an indication that a gene responsible for pathogenicity has been inactivated. The positions of the inactivating mutations are then identified using standard methods (e.g., by polymerase chain reaction and sequencing of insertion/transposon junctions or by mapping) leading to the cloning and identification of the mutated virulence factor(s) (e.g., by nucleotide sequencing).

In another working example, pathogenesis is assayed by monitoring colonization of the nematode intestine, two to eight *C. elegans* worms (e.g., L4 hermaphrodite larvae) are placed on a lawn of mutagenized *Salmonella typhimurium* strain LT2, prepared from a mutagenic library, expressing a detectable marker (e.g., GFP) for an appropriate period of time and then transferred to plates for feeding on non-pathogenic bacteria (e.g., *E. coli*/DH5alpha). Strain LT2 is mutated according to standard methods. After approximately five hours worms are examined for the presence of the pathogen in the intestine using confocal microscopy. Worms feeding on wild-type, pathogenic *S. typhimurium* strain LT2, will present bacteria growing and proliferating in the gut. Worms feeding on mutated LT2 that contain a mutation in a gene that enables the establishment of a persistent infection will present a reduced, non-proliferating population in the gut. Thus, the absence or reduced presence of mutated LT2 in the worm intestine is taken as an indication that a gene responsible for pathogenicity has been inactivated. The mutated virulence factor is then identified using standard methods.

Compound Screening Assays

As discussed above, our experimental results demonstrated that virulence factors are involved in pathogenicity of the nematode, *C. elegans*. Based on this discovery we have also developed a screening procedure for identifying therapeutic compounds (e.g., anti-pathogenicity pharmaceuticals) which can be used to inhibit the ability of a pathogen to persistently infection. In general, the method involves screening any number of compounds for therapeutically-active agents by employing the Salmonellae/nematode killing system described herein. Based on our demonstration that these pathogens infect and kill *C. elegans*, it will be readily understood that a compound which interferes with the pathogenicity of a pathogen (e.g., a salmonellae pathogen) in a nematode also provides an effective therapeutic agent in a mammal (e.g., a human patient). Whereas most antibiotics currently in medical use are either bactericidal or bacteriostatic, thus favoring resistant strains or mutants, the compounds identified in the screening procedures described herein do not kill the bacteria or prevent their growth in vitro, but instead render them non-pathogenic. Moreover, since the screening procedures of the invention are performed in vivo, it is also unlikely that the identified compounds will be highly toxic to the host organism.

Accordingly, the methods of the invention simplify the evaluation, identification, and development of active agents such as drugs for the treatment of pathogenic diseases caused by microbes that can establish a long lasting association or persistent infection with a nematode.

In general, the chemical screening methods of the invention provide a straightforward means for selecting natural product extracts or compounds of interest from a large population which are further evaluated and condensed to a few active and selective materials. Constituents of this pool are then purified and evaluated in the methods of the invention to determine their anti-pathogenic activity.

Text Extracts and Compounds

In general, novel anti-pathogenic drugs are identified from large libraries of both natural product or synthetic (or semi-synthetic) extracts or chemical libraries according to methods known in the art. The screening method of the present invention is appropriate and useful for testing compounds from a variety of sources for possible anti-pathogenic activity. The initial screens may be performed using a diverse library of compounds, but the method is suitable for a variety of other compounds and compound libraries. Such compound libraries can be combinatorial libraries, natural product libraries, or other small molecule libraries. In addition, compounds from commercial sources can be tested, as well as commercially available analogs of identified inhibitors.

For example, those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have anti-pathogenic activity, further fractionation of the positive lead extract is necessary to isolate chemical constituents responsible for the observed effect. Thus, the goal of the extraction, fractionation, and purification process is the careful characterization and identification of a chemical entity within the crude extract having anti-pathogenic activity. Methods of fractionation and purification of such heterogenous extracts are known in the art. If desired, compounds shown to be useful agents for the treatment of pathogenicity are chemically modified according to methods known in the art.

Since many of the compounds in libraries such as combinatorial and natural products libraries, as well as in natural products preparations, are not characterized, the screening methods of this invention provide novel compounds which are active as inhibitors or inducers in the particular screens, in addition to identifying known compounds which are active in the screens. Therefore, this invention includes such novel compounds, as well as the use of both novel and known compounds in pharmaceutical compositions and methods of treating.

Exemplary High Throughput Screening Systems

To evaluate the efficacy of a molecule or compound in promoting host resistance to, or inhibiting pathogenicity of, a number of high throughput assays may be utilized.

For example, to enable mass screening of large quantities of natural products, extracts, or compounds in an efficient and systematic fashion, *Caenorhabditis elegans*, (e.g., oneday-old adult hermaphrodite worms, an L4 hermaphrodite larvae or a mutant worm such as aex-2, unc-25, phm-2, eat-14, pgp-4, or mrp-1), are cultured in wells of a microtiter plate, facilitating the semiautomation of manipulations and full automation of data collection. As is discussed above, salmonellae pathogens establish a persistent infection, including a long-lasting association that kills *C. elegans*. If a salmonellae pathogen has diminished pathogenicity, then adult or L4 worms live, develop into adult hermaphrodites, and produce thousands of live progeny. Accordingly, if *C. elegans* is incubated with the pathogen, the worms will die, unless a compound is present to reduce pathogenicity. The presence of such live progeny is easily detected using a variety of methods, including visual screening with standard microscopes.

To evaluate the ability of a test compound or extract to promote a host's resistance to a pathogen or to repress pathogenicity of a pathogen, a test compound or extract is inoculated at an appropriate dosage into an appropriate agar medium seeded with an appropriate amount of an overnight culture of a pathogen, e.g., *S. typhimurium* strain LT2. If desired, various concentrations of the test compound or extract can be inoculated to assess dosage effect on both the host and the pathogen. Control wells are inoculated with non-pathogenic bacteria (negative control) or a pathogen in the absence of a test compound or extract (positive control). Plates are then incubated 24 hours at 37° C. to facilitate the growth of the pathogen. Microtiter dishes are subsequently cooled to 25° C., and two *C. elegans* L4 hermaphrodite larva expressing a detectable marker such as GFP are added to the plate and incubated at 25° C., the upper limit for normal physiological integrity of *C. elegans*. At an appropriate time interval, e.g., five hours, wells are examined for surviving worms, the presence of progeny, or both, e.g., by visual screening or monitoring motion of worms using a motion detector, or monitoring the fluorescence of the nematodes.

In another working example, the presence of a persistent infection in the gut of *C. elegans* is carried out as follows. Media is prepared as described herein and a test compound or compound library is also added. On the tissue culture plate, approximately eight worms, at the one-day old adult stage, are placed on the lawn of pathogenic bacteria expressing a detectable markers such as GFP from a plate of OP50 *E. coli*. The plates are incubated at 25° C. for 5 hours and then the worms are transferred to a plate of OP50 *E. coli* not expressing GFP. After 24 hours, the worms are examined by fluorsecent microcopy for the presence of the pathogen in the worm intestine. Each experimental condition is done in triplicate and repeated at least twice. Test compounds that reduce the presence the pathogen in the worm intestine are taken as being useful for treating microbial infection.

Comparative studies between treated and control worms (or larvae) are used to determine the relative efficacy of the test molecule or compound in promoting the host's resistance to the pathogen or inhibiting the establishment of a persistent infection. A test compound which effectively stimulates, boosts, enhances, increases, or promotes the host's resistance to the pathogen or which inhibits, inactivates, suppresses, represses, or controls pathogenicity of the pathogen, and does not significantly adversely affect the normal physiology, reproduction, or development of the worms is considered useful in the invention.

Use

The methods of the invention provide a simple means for identifying virulence factors that enable a pathogen to establish a persistent infection in a nematode and compounds capable of either inhibiting pathogenicity or enhancing an organism's resistance capabilities to such pathogens. Accordingly, a chemical entity discovered to have medicinal value using the methods described herein are useful as either drugs, or as information for structural modification of existing anti-pathogenic compounds, e.g., by rational drug design.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections which provide continuous, sustained levels of the drug in the patient. Treatment of human patients or other animals will be carried out using a therapeutically effective amount of an anti-pathogenic agent in a physiologically-acceptable carrier. In the context of treating a bacterial infection a "therapeutically effective amount" or "pharmaceutically effective amount" indicates an amount of an antibacterial agent, e.g., as disclosed for this invention, which has a therapeutic effect. This generally refers to the inhibition, to some extent, of the normal cellular functioning of bacterial cells (e.g., salmonellae cells) causing or contributing to a bacterial infection. The dose of antibacterial agent which is useful as a treatment is a "therapeutically effective amount." Thus, as used herein, a therapeutically effective amount means an amount of an antibacterial agent which produces the desired therapeutic effect as judged by clinical trial results, standard animal models of infection, or both. This amount can be routinely determined by one skilled in the art and will vary depending upon several factors, such as the particular bacterial strain involved and the particular antibacterial agent used. This amount can further depend on the patient's height, weight, sex, age, and renal and liver function or other medical history. For these purposes, a therapeutic effect is one which relieves to some extent one or more of the symptoms of the infection and includes curing an infection.

The compositions containing antibacterial agents of virulence factors or genes can be administered for prophylactic or therapeutic treatments, or both. In therapeutic applications, the compositions are administered to a patient already suffering from an infection from bacteria (similarly for infections by other microbes), in an amount sufficient to cure or at least partially arrest the symptoms of the infection. An amount adequate to accomplish this is defined as "therapeutically effective amount." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to, or otherwise at risk of, a particular infection. Such an amount is defined to be a "prophylactically effective amount." In this use, the precise amounts again depend on the patient's state of health, weight, and the like. However, generally, a suitable effective dose will be in the range of 0.1 to 10000 milligrams (mg) per recipient per day, preferably in the range of 10–5000 mg per day. The desired dosage is preferably presented in one, two, three, four, or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 25 mg/kg of patient body weight, between about one to four times per day.

Suitable carriers and their formulation are described, for example, in Remington's *Pharmaceutical Sciences* by E. W. Martin. The amount of the anti-pathogenic agent to be administered varies depending upon the manner of administration, the age and body weight of the patient, and with the type of disease and extensivenss of the disease. Generally, amounts will be in the range of those used for other agents used in the treatment of other microbial diseases, although in certain instances lower amounts will be needed because of the increased specificity of the compound. A compound is administered at a dosage that inhibits microbial proliferation.

All publications and patents mentioned in this specification are herein incorporated by reference to the same extent as if each individual publication or patent was specifically and individually indicated to be incorporated by reference.

From the foregoing description, one skilled in the art can easily ascertain the essential characteristics of this invention, can make various changes and modifications of the invention to adapt it to various usages and conditions. Thus, other embodiments are also within the claims.

What is claimed is:

1. An isolated *Caenorhabditis elegans* nematode infected with an isolated *Salmonella typhimurium* bacterium.

2. The nematode of claim 1, wherein said bacterium expresses a detectable marker.

3. The nematode of claim 1, wherein said nematode is a one-day old adult hermaphrodite or an L4 larval stage worm.

4. The nematode of claim 1, wherein said bacterium colonizes the intestine of said nematode.

5. The nematode of claim 1, wherein said *S. typhimurium* bacterium is *S. typhimurium* strain SL1344.

6. A method of screening for a compound that inhibits a *S. typhimurium* bacterium in a *C. elegans* nematode, comprising the steps of:
    (a) providing a *C. elegans* nematode infected with a *S. typhimurium* bacterium;
    (b) contacting said infected *C. elegans* nematode with a test compound; and
    (c) determining whether the test compound inhibits said *S. typhimurium* bacterium in said infected *C. elegans* nematode.

7. The method of claim 6, wherein said bacterium expresses a detectable gene product.

8. The nematode of claim 6, wherein said nematode is a one-day old adult hermaphrodite or an L4 larval stage worm.

9. The nematode of claim 6, wherein colonization of the intestine of said nematode by said bacterium is decreased.

10. The method of claim 6, wherein said bacterium is *S. typhimurium* strain SL1344.

11. The method of claim 6, wherein said test compound is provided in a compound library.

12. The method of claim 6, wherein said test compound is a small organic compound.

13. The method of claim 6, wherein said determining step is measured by killing of *C. elegans* by a *S. typhimurium* bacterium.

14. The method of claim 13, wherein said bacterium causes less *C. elegans* killing in the presence of said test compound than in the absence of said test compound.

15. A method of screening for a compound that inhibits *S. typhimurium* bacterial infection in a *C. elegans* nematode, comprising the steps of:
    (a) providing a *C. elegans* nematode infected with a *S. typhimurium* bacterium expressing a detectable marker;
    (b) contacting said infected *C. elegans* nematode with a test compound; and
    (c) determining whether said *S. typhimurium* bacterium infects said *C. elegans* nematode by measuring the level of detectable marker in said nematode, where a decrease of the marker in said *C. elegans* nematode indicates that said test compound inhibits a *S. typhimurium* bacterial infection in the nematode.

\* \* \* \* \*